United States Patent
Kristensen

(10) Patent No.: US 11,672,413 B2
(45) Date of Patent: Jun. 13, 2023

(54) ARTICULATED TIP PART FOR AN ENDOSCOPE

(71) Applicant: AMBU A/S, Ballerup (DK)

(72) Inventor: Jakob Bønnelykke Kristensen, Ølstykke (DK)

(73) Assignee: AMBU A/S, Ballerup (DK)

( * ) Notice: Subject to any disclaimer, the term of this patent is extended or adjusted under 35 U.S.C. 154(b) by 822 days.

(21) Appl. No.: 16/496,708

(22) PCT Filed: Mar. 26, 2018

(86) PCT No.: PCT/EP2018/057599
§ 371 (c)(1),
(2) Date: Sep. 23, 2019

(87) PCT Pub. No.: WO2018/172565
PCT Pub. Date: Sep. 27, 2018

(65) Prior Publication Data
US 2020/0113415 A1      Apr. 16, 2020

(30) Foreign Application Priority Data

Mar. 24, 2017   (DK) .......................... PA 2017 70215

(51) Int. Cl.
*A61B 1/005*      (2006.01)
*A61B 1/00*       (2006.01)
(Continued)

(52) U.S. Cl.
CPC .......... *A61B 1/0055* (2013.01); *A61B 1/0011* (2013.01); *A61B 1/0057* (2013.01);
(Continued)

(58) Field of Classification Search
CPC ... A61B 1/0055; A61B 1/0011; A61B 1/0057; B29C 45/0053; B29C 45/14336;
(Continued)

(56) References Cited

U.S. PATENT DOCUMENTS 3,800,021 A    3/1974   Monett et al.
4,580,551 A    4/1986   Siegmund et al.
(Continued)

FOREIGN PATENT DOCUMENTS

EP    0 183 585        6/1986
EP    2524645 A1      11/2012
(Continued)

OTHER PUBLICATIONS

International Search Report and Written Opinion in related PCT application No. PCT/EP2018/057599 dated Jun. 29, 2018, 9 pages.
(Continued)

*Primary Examiner* — Aaron B Fairchild
(74) *Attorney, Agent, or Firm* — Faegre Drinker Biddle & Reath LLP

(57) ABSTRACT

An articulated tip part suitable for an endoscope, where the articulated tip part includes a distal end segment, a proximal end segment and a number of intermediate segments arranged between the distal end segment and the proximal end segment, the segments being joined together to form an articulated assembly of segments, a passage running along the length of the articulated tip part, and a bending element, the bending element being fastened to at least two segments and being arranged along a path which is essentially parallel to a centerline of the articulated tip part.

18 Claims, 8 Drawing Sheets

(51) Int. Cl.
  *B29C 45/00* (2006.01)
  *B29C 45/14* (2006.01)
  *A61M 25/00* (2006.01)
  *B29L 31/00* (2006.01)

(52) U.S. Cl.
  CPC .... *B29C 45/0053* (2013.01); *B29C 45/14336* (2013.01); *B29C 45/14467* (2013.01); *A61M 25/0074* (2013.01); *B29C 2045/0077* (2013.01); *B29L 2031/7546* (2013.01)

(58) Field of Classification Search
  CPC ...... B29C 45/14467; B29C 2045/0077; A61M 25/0074; B29L 2031/7546
  See application file for complete search history.

(56) References Cited

U.S. PATENT DOCUMENTS

| | | | |
|---|---|---|---|
| 4,651,718 A | 3/1987 | Collins | |
| 4,706,653 A | 11/1987 | Yamamoto | |
| 4,745,470 A | 5/1988 | Yabe et al. | |
| 4,778,247 A | 10/1988 | Carpenter | |
| 4,832,003 A | 5/1989 | Yabe | |
| 4,856,495 A | 8/1989 | Tohjoh et al. | |
| 4,860,732 A | 8/1989 | Hasegawa et al. | |
| 4,911,148 A | 3/1990 | Sosnowski et al. | |
| 4,918,521 A | 4/1990 | Yabe et al. | |
| 5,089,895 A | 2/1992 | Fraker et al. | |
| 5,176,126 A * | 1/1993 | Chikama | A61B 1/0055 604/95.04 |
| 5,376,960 A | 12/1994 | Wurster | |
| 5,379,756 A | 1/1995 | Pileski et al. | |
| 5,418,566 A | 5/1995 | Kameishi | |
| 5,438,975 A | 8/1995 | Miyagi et al. | |
| 5,547,457 A | 8/1996 | Tsuyuki et al. | |
| 5,830,401 A | 11/1998 | Prichard et al. | |
| 5,966,168 A | 10/1999 | Miyazaki | |
| 6,004,263 A | 12/1999 | Nakaichi | |
| 6,110,104 A | 8/2000 | Suzuki et al. | |
| 6,302,616 B1 | 10/2001 | Takahashi | |
| 6,456,863 B1 | 9/2002 | Levin et al. | |
| 7,455,806 B2 | 11/2008 | Junger et al. | |
| 7,578,786 B2 | 8/2009 | Boulais et al. | |
| 7,758,495 B2 | 7/2010 | Pease et al. | |
| 8,182,422 B2 | 5/2012 | Bayer et al. | |
| 8,547,424 B2 | 10/2013 | Ishii et al. | |
| 8,591,404 B2 | 11/2013 | Yamazaki | |
| 8,803,960 B2 | 8/2014 | Sonnenschein et al. | |
| 10,149,608 B2 | 12/2018 | Fujitani | |
| 10,312,804 B2 | 6/2019 | Ohshima | |
| 10,321,804 B2 | 6/2019 | Jacobsen et al. | |
| 2002/0193663 A1 | 12/2002 | Matsuura | |
| 2003/0056540 A1 | 3/2003 | Mukasa et al. | |
| 2003/0229420 A1 * | 12/2003 | Buckingham | A61B 34/30 700/245 |
| 2004/0199052 A1 | 10/2004 | Banik et al. | |
| 2004/0242963 A1 | 12/2004 | Matsumoto | |
| 2005/0070759 A1 | 3/2005 | Armstrong | |
| 2005/0075538 A1 | 4/2005 | Banik et al. | |
| 2005/0131279 A1 | 6/2005 | Boulais | |
| 2005/0140068 A1 | 6/2005 | Junger et al. | |
| 2005/0154262 A1 | 7/2005 | Banik et al. | |
| 2005/0119527 A1 | 9/2005 | Ellis et al. | |
| 2005/0203341 A1 | 9/2005 | Welker et al. | |
| 2005/0234499 A1 | 10/2005 | Olson et al. | |
| 2006/0178556 A1 | 8/2006 | Hasser et al. | |
| 2007/0049800 A1 | 3/2007 | Boulais | |
| 2007/0129466 A1 | 6/2007 | Kagawa et al. | |
| 2007/0249896 A1 | 10/2007 | Goldfarb et al. | |
| 2007/0249907 A1 | 10/2007 | Boulais | |
| 2008/0194911 A1 | 8/2008 | Lee | |
| 2008/0214897 A1 | 9/2008 | Matsuo | |
| 2008/0221393 A1 | 9/2008 | Padget | |
| 2008/0249483 A1 | 10/2008 | Slenker | |
| 2008/0268559 A1 | 10/2008 | Jung | |
| 2008/0287741 A1 | 11/2008 | Ostrovsky | |
| 2009/0054728 A1 | 2/2009 | Trusty | |
| 2009/0177040 A1 | 7/2009 | Lyons | |
| 2009/0209819 A1 | 8/2009 | Kitagawa et al. | |
| 2009/0242115 A1 * | 10/2009 | Ito | A61B 1/0055 156/293 |
| 2010/0160735 A1 * | 6/2010 | Bakos | A61B 17/3417 600/141 |
| 2010/0210905 A1 | 8/2010 | Takeuchi et al. | |
| 2010/0217082 A1 | 8/2010 | Ito et al. | |
| 2010/0280316 A1 | 11/2010 | Dietz et al. | |
| 2010/0324367 A1 | 12/2010 | Matsumoto et al. | |
| 2011/0034771 A1 * | 2/2011 | Konstorum | A61B 1/0055 600/141 |
| 2011/0230718 A1 | 9/2011 | Akui | |
| 2011/0251519 A1 | 10/2011 | Romoscanu | |
| 2012/0002981 A1 | 2/2012 | Frassica et al. | |
| 2012/0165608 A1 | 6/2012 | Banik et al. | |
| 2014/0114129 A1 | 4/2014 | Peh | |
| 2015/0366436 A1 | 12/2015 | Iuel | |
| 2015/0374211 A1 * | 12/2015 | Smith | A61B 17/3421 600/114 |
| 2016/0101254 A1 | 4/2016 | Hansen | |

FOREIGN PATENT DOCUMENTS

| | | |
|---|---|---|
| WO | 2010066790 A1 | 6/2010 |
| WO | 2012150897 A1 | 11/2012 |

OTHER PUBLICATIONS

European search report of related European Application No. 18 718 706.7, dated May 24, 2022, 4 pages.

First examination report of related Danish Application No. PA2017 70215 dated Mar. 22, 2018, 9 pages.

* cited by examiner

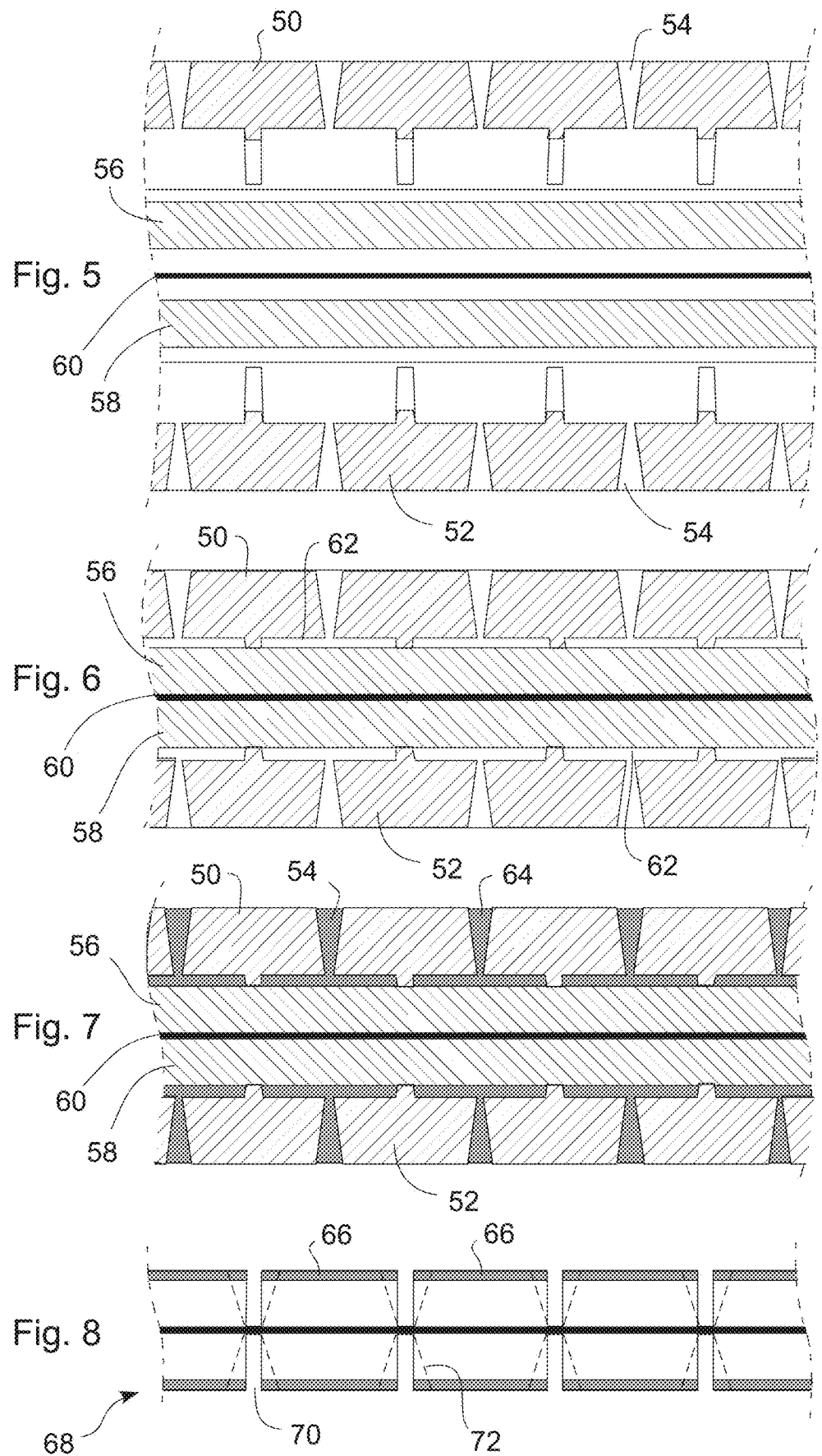

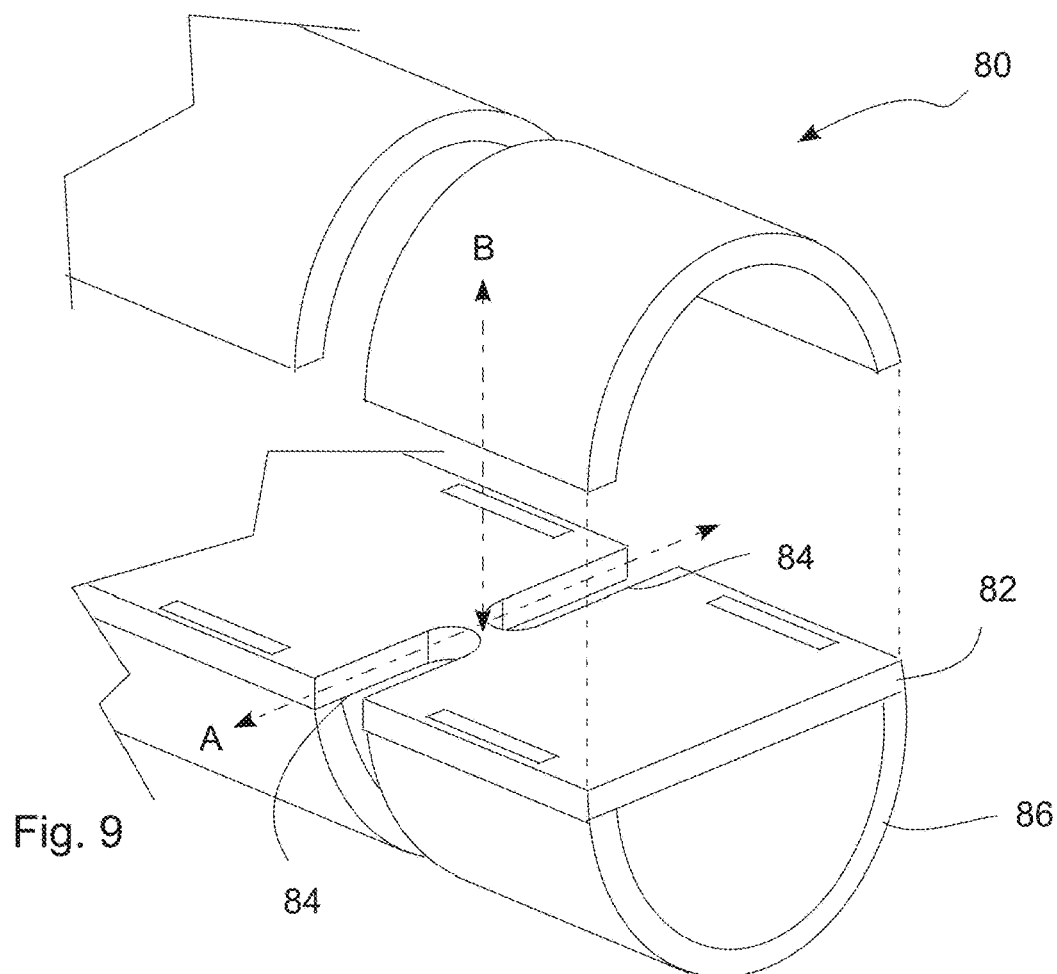
Fig. 9
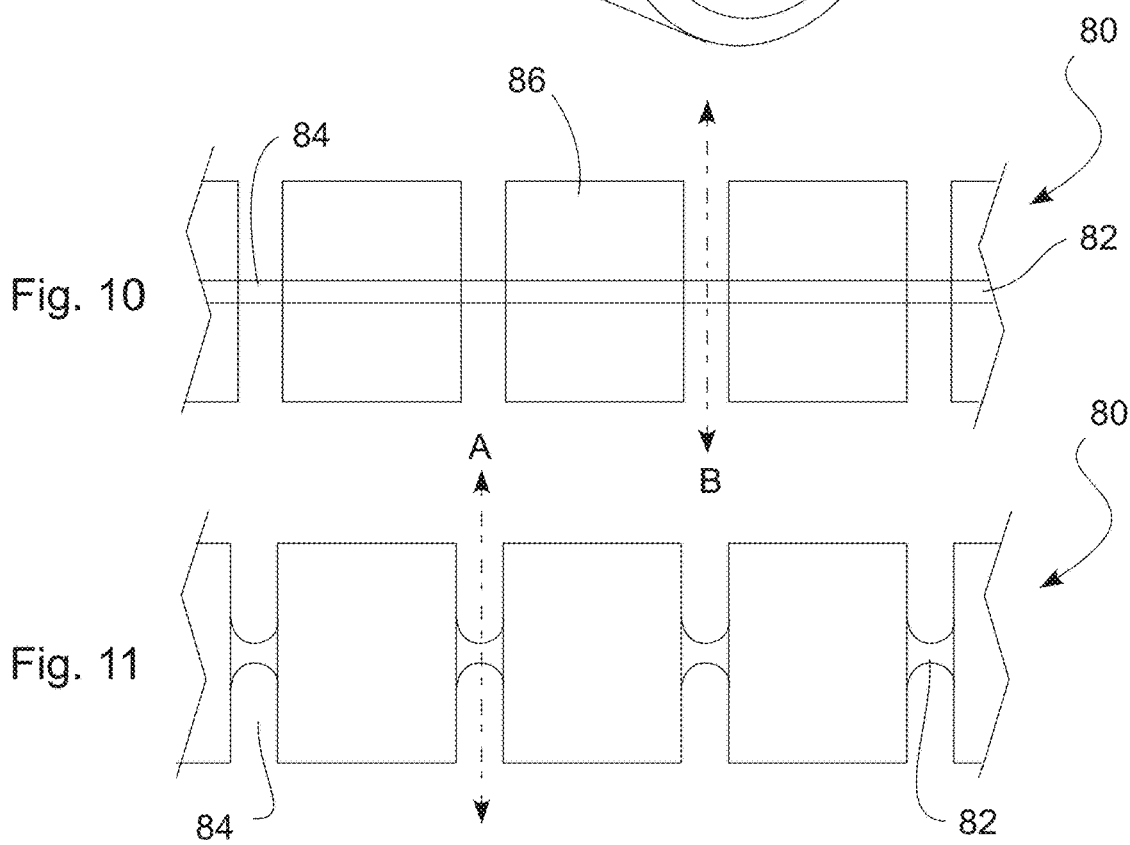
Fig. 10
Fig. 11

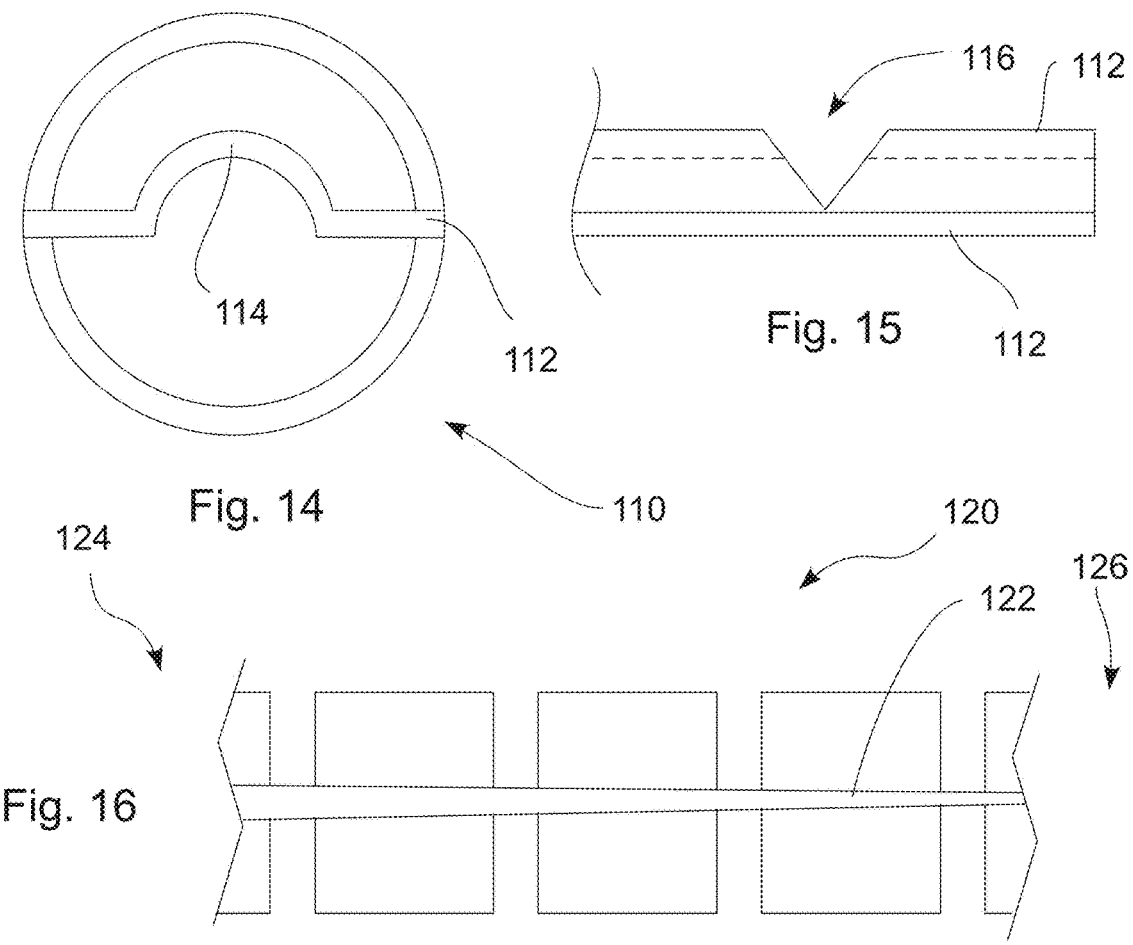
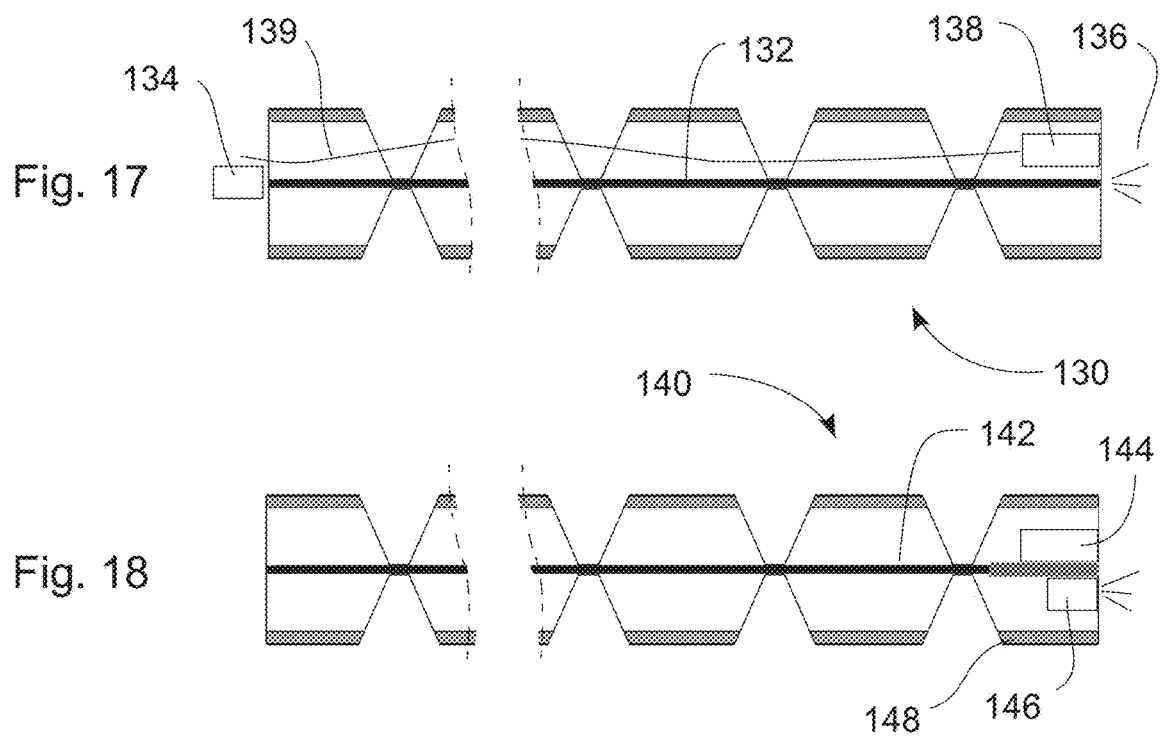

ARTICULATED TIP PART FOR AN ENDOSCOPE

CROSS-REFERENCE TO RELATED APPLICATIONS

This application is a National stage application filed under 35 U.S.C. § 371 of International Application No. PCT/EP2018/057599, filed on Mar. 26, 2018, which claims the benefit of Denmark Patent Application No. PA 2017 70215, filed on Mar. 24, 2017, which applications are incorporated herein by reference thereto.

TECHNICAL FIELD

The current invention relates to an articulated tip part suitable for an endoscope where the articulated tip part comprises an articulated assembly of segments and a passage running along the length of the articulated tip part.

DESCRIPTION OF RELATED ART

Endoscopes are well known devices for visually inspecting inaccessible places such as human body cavities. Typically, endoscopes comprise an elongated insertion tube with a handle at the proximal end as seen from the operator and visual inspections means, such as a built in camera, at the distal end of the elongated insertion tube. Electrical wiring for the camera and other electronics such as LED lighting run along the inside of the elongated insertion tube from the handle to the tip at the distal end. Instead of using cameras, endoscopes may also be fibre-optic, in which case the optical fibres run along the inside of the elongated insertion tube.

In order to be able to manoeuvre the endoscope inside the body cavity, the distal end of the endoscope may comprise a section with increased flexibility, allowing the operator to bend this section. This section is, in the current specification, called an "articulated tip part", but it could also be called other suitable names, for example "bending section". Typically, the bending action is activated by tensioning or slackening pull wires also running along the elongated insertion tube from the articulated tip part to a control mechanism located at the handle. Furthermore, in some cases, a working channel may also run along the inside of the insertion tube from the handle to the tip, e.g. allowing liquid to be removed from the body cavity or allowing the insertion of surgical instruments or the like into the body cavity.

Different types of articulated tip parts for endoscopes have been known for a number of years. Typically, endoscopes have been complicated and expensive devices that were used for multiple patients with a sterilization procedure occurring between using the endoscope on different patients. Articulated tip parts for these types of endoscopes have typically been assembled from multiple segments linked together with small hinges.

However, recently endoscopes have been introduced which are disposable or one time use only endoscopes. These endoscopes are only used for a single patient and they therefore do not have to be sterilized between uses. Articulated tip parts for these types of endoscopes need to be cheaper and simpler to assemble due to the lower cost of the final device and the higher number of units produced.

As such a number of new types of articulated tip parts for endoscopes have been introduced in the last few years. For example, U.S. Publ. No. 2015/0335227 discloses an articulated tip part for an endoscope comprising an integrally moulded web between bending segments of the articulated tip part wherein the web and bending segments are moulded as one part.

U.S. Publ. No. 2013/0158355 also discloses an articulated tip part for an endoscope comprising two way flexible plastic members connecting individual segments of the articulated tip part.

U.S. Publ. No. 2008/0051802 schematically discloses a large number of different embodiments of articulated tip parts for endoscopes.

U.S. Pat. No. 4,911,148 discloses a fibre-optic endoscope with an articulated tip part. The articulated tip part is an integrally moulded member with spaced apart cut-outs progressively increasing in size towards the distal end. The cut-outs are provided in one side only, thus only allowing the bending of the articulated tip part in one direction.

U.S. Publ. No. 2004/0199052 discloses some different embodiments of articulated tip parts, some of which comprise an integrally moulded construction.

U.S. Pat. No. 5,176,126 discloses an articulated tip part which comprises a central bending part with a number of circular discs which are snapped onto the central bending part. In this case a rather complex mechanism is provided which is complicated and time consuming to assemble. Furthermore, if the bending section is squeezed, the discs could disengage with the bending element resulting in a deformed bending section.

EP2524645 discloses an articulated tip part for an endoscope comprising a number of spaced apart discs connected together by a bending unit glued or welded to the discs.

While articulated tip parts for endoscopes are well known in the art, there are still possibilities to further improve articulated tip parts for endoscopes.

SUMMARY OF THE INVENTION

A first aspect of the current invention is to provide an articulated tip part as mentioned in the introductory paragraph which allows for a more flexible manufacturing procedure.

A second aspect of the current invention is to provide an articulated tip part as mentioned in the introductory paragraph which allows more functionality to be built into the articulated tip part in a simple and fast manner during manufacturing of the articulated tip part.

A third aspect of the current invention is to provide an articulated tip part as mentioned in the introductory paragraph which allows the properties of the articulated tip part to be adjusted in a simple manner.

These aspects are provided at least in part by an articulated tip part as mentioned in the introductory paragraph where the articulated tip part further comprises a bending element, said bending element being fastened to at least two segments and being arranged along a path which is essentially parallel to a centre line of the articulated tip part. By providing a bending element which is fastened to the segments it is possible to easily change the properties of the articulated tip portion simply by adjusting the properties of the bending element.

In certain cases, the term "fastened to" could be understood as implying that the bending element is separately identifiable from the segments. In certain cases, the term "fastened to" could be understood as implying that the bending element is made of a different material than the segments.

In one embodiment, the bending element could be fastened to at least three segments and the segments could comprise an inner surface facing the centreline of the passage and an outer surface facing away from the centreline of the passage, said bending element could furthermore be accessible via the inner and/or the outer surface. The phrase "accessible via" should be understood in this specification as in that it would be possible to see and/or come into contact with the bending element from either the inner and/or the outer surface without damaging the inner and/or outer surface respectively. When the bending element is accessible in this way, it is possible to hold the bending element during manufacturing in a stable and easy manner.

In one embodiment, the bending element could extend past the inner surface of the segments and towards the centre line of the passage and/or past the outer surface of the segments and away from the centre line of the passage. In both these cases, it would be possible to hold the bending element in a simple manner during manufacturing.

In one embodiment, the bending element could comprise recesses 38 having a depth with a main component which is perpendicular to the longitudinal extension of the bending element and the material 28c of the segments could extend into the recesses 38, as seen in FIGS. 4A and 4B. In one embodiment, the depth of the recesses could have a main component which is perpendicular to the main surface of the bending element. In one embodiment, the depth of the recesses could have a main component which is perpendicular to a plane which is essentially parallel to the main surface of the bending element. In one embodiment, the bending element comprises recesses on opposite surfaces of the bending element, for example top and bottom. In one embodiment, said recesses are extending towards each other.

In one embodiment, the bending element could comprise protrusions 38a having a height which has a component which is perpendicular to the longitudinal extension of the bending element and in that the protrusions extend into the material of the segments, e.g. recesses 28d, as seen in FIGS. 4C and 4D. In one embodiment, the height of the protrusions could have a component which is perpendicular to the main surface of the bending element. In one embodiment, the height of the protrusions could have a component which is perpendicular to a plane which is essentially parallel to the main surface of the bending element. In one embodiment, the bending element comprises protrusions on opposite surfaces of the bending element, for example top and bottom. In one embodiment said recesses are extending away from each other.

In both the case with recesses and the case with protrusions, a stronger mechanical link is formed between the segments and the bending element. This will especially help with ensuring that the segments do not slide along the bending element. Furthermore, depending on the design of the recesses and/or protrusions, they will also help prevent the segments from detaching from the bending element in case the bending section is compressed. In certain cases an embodiment could be provided with both recesses and protrusions.

In one embodiment, the recesses could be arranged to pass completely through the bending element such that the material of the segments can pass through the bending element. In this way, the segments get very strongly linked with the bending element in a simple manner. In one embodiment, the recesses could be formed as through going holes with a closed perimeter such that the material of the bending element completely encircles the portion of the material of a segment passing through the bending element.

In a similar way, in one embodiment, protrusions could be used which have a form which make a positive connection to the material of the segments. For example, a base portion 38c of the protrusion is smaller than the tip portion 38b of the protrusion, as seen in FIG. 4E. In one case it could be said that the protrusions are embedded in the material of the segments. In this way, it becomes difficult to pull the segments away from the bending element since a mechanical connection is made between the segments and the bending element.

In one embodiment, each segment is engaged with four recesses in the bending element, two recesses arranged on an inner surface of the bending element facing the centreline of the passage and two recesses arranged on an outer surface of the bending element facing away from the centreline of the passage.

In one embodiment, the segments could comprise a first part arranged on a first side of the bending element and a second part arranged on a second side of the bending element and the first and second part could be connected via the recesses which pass through the bending element. In one embodiment, the two parts of the segments could be formed with corresponding engagement means which connect through the recesses. In one embodiment the engagement means could be corresponding snap mechanisms which can be snapped together through the recess. In one embodiment, the first and second parts could each be provided with engagement means which engage with corresponding engagement means provided in the bending element. For example, in one embodiment, engagement means on a first part engage with a recess in the bending element and engagement means on a second part also engage with the recess in the bending element. In one embodiment, the first and second parts could be integrally formed through the recesses in the bending element. This could be the case in a moulding method where the segments are moulded around the bending element. In this way, the moulding material could flow through the recesses and the first and second parts would therefore be integrally formed and thereby strongly fastened to the bending element.

In one embodiment, the bending element could be arranged such that one of the at least two or at least three segments is the proximal segment or such that one of the at least two or at least three segments is the distal segment. In these situations, the bending element would therefore be embedded in at least the proximal or the distal segment. In one embodiment, a single bending element could be fastened to the proximal, the distal and all the intermediate segments. This can provide for a simple manufacturing process since only a single bending element needs to be formed and connected to the segments.

In one embodiment, a dimension of the bending element which is perpendicular to the longitudinal extension of the bending element could be greater than the minimum inside diameter of the passage. In this case, the bending element can span the passage. In one embodiment, the bending element could be engaged with both opposing inside surfaces of the segments. In this case, the bending element can also provide strength to the articulated tip part and reduce the deformation of the segments should the segments be compressed.

In one embodiment, the bending element could comprise a light guide fastened to and running along the length of the bending element. By integrating a light guide or other functional elements into the bending element, these functional elements can be placed in the articulated tip part in a simple manner during the initial manufacturing of the articulated tip part and do therefore not have to be separately assembled into the tip part later on.

In one embodiment the bending element could comprise a flex print portion or flexible printed circuit board fastened to and running along the length of the bending element. In one embodiment, the bending element could comprise electronic components fastened to and spaced along the length of the bending element. In one embodiment a light guide and a flex print portion could be integrated together.

In one embodiment the stiffness of the bending element could vary along the longitudinal extension of the bending element. In this way a custom bending profile could be defined. In one embodiment the thickness of the bending element perpendicular to the longitudinal extension of the bending element could change along the length of the bending element. In one embodiment the bending element could be an extruded element. In one embodiment the bending element could have a non-planar cross section. In one embodiment the bending element could be provided with spaced apart weakened portions arranged along the longitudinal extension of the bending element. In certain cases, such weakened portions could have a lower stiffness than the remainder of the bending element. In some cases, these weakened portions could allow pivotal motion of the segments in a plane parallel to the bending element. In certain cases, such weakened portions could be provided in the form of cut-outs in the material of the bending element. In one embodiment, the cut-outs could be symmetrical cut-outs made at spaced apart intervals along both side edges of the bending element. In one embodiment the bending element could be a laminated element comprising different layers having different functions.

While the main contribution of the current invention is to provide a novel articulated tip part for an endoscope, the scope of protection should also cover an endoscope comprising an articulated tip part as defined in this specification. In certain cases, the endoscope could be a single use or a disposable endoscope. In certain cases, the endoscope could be an endoscope suitable for use in a hospital or other medical related setting. The scope of protection should also extend to a package suitable for use in a hospital or medical setting comprising an endoscope with an articulated tip part according to the current specification.

Likewise, while the main focus of this specification is on providing a novel articulated tip part product, the specification also discloses some methods of manufacturing an articulated tip part. In certain cases, the method itself is novel and inventive. In one embodiment of a suitable method, the following steps could be implemented: a) opening an injection mould, b) inserting a bending element into the injection mould c) closing the injection mould, d) injecting hot melted material into the injection mould, e) allowing the injection mould to cool until the hot melted material has solidified, f) opening the injection mould, and g) removing the articulated tip portion from the injection mould. In this way, a simple manufacturing method for joining the segments with a bending element(s) is provided. It should also be noted that while some of the embodiments of the articulated tip part product described above could be limited to embodiments where at least three segments are connected with a bending element, the method as disclosed here should be broad enough to cover a situation where at least two segments are joined with a bending element.

In one embodiment of the method, after removing the articulated tip portion from the injection mould, a portion of the bending element could be trimmed from the articulated tip portion. This trimmed portion could be used during the manufacturing procedure to hold the bending element in place.

In one embodiment of the method, step b) could comprise a step where a plurality of bending elements are inserted into the injection mould. In one case, the plurality of bending elements could connect a plurality of segments in the final injection moulded product.

In one embodiment, the method could further comprise the steps of inserting a central core into the injection mould prior to injecting the hot melted material, and then removing the central core from the injection moulded portion of the articulated tip part after the hot melted material has cooled. The central core can be arranged to form or define a passage through the resulting injection moulded articulated tip part once the core is removed. In one embodiment, the central core could be withdrawn in a direction which is parallel to the longitudinal extension of the articulated tip part. In one embodiment, a core could be used to form the channels for the passage and/or the channels for the pull wires.

In one embodiment, the central core could be arranged to hold the bending element in place in the mould prior to injecting hot melted material into the injection mould. In one embodiment, the central core could also be used to insert the bending element into the mould. In one embodiment, the central core could comprise at least two parts and the bending element could be held in place between the two parts of the central core.

It should be noted that in the claims as filed, focus is directed to a product comprising a bending element and a number of segments. Likewise focus is directed to a method using in mould manufacturing techniques where the bending element is integrated with the segments of the articulated tip part directly in the injection mould.

However, the current specification also discloses a number of additional inventions which could form the basis of one or more divisional applications. In particular, the specification discloses an invention directed to a method of assembling an articulated tip part as disclosed in this specification where the individual parts of the articulated tip part are manufactured individually and then assembled together. In particular this method comprises the steps of providing a bending element and a number of segment portions and then fastening the segment portions to the bending element. In one embodiment, the segments are provided as a top part and a bottom part and the top part is fastened to a top surface of the bending element and the bottom part is fastened to a bottom surface of the bending element. In one embodiment, the bending element is held in a fixed position by a clamping mechanism during the assembly of the segments on the bending element.

Another invention could be directed to an articulated tip portion comprising a bending element in the form of a foil like element and a number of segments arranged along the bending element and where each segment comprises two parts, one placed on each side of the bending element. Another invention could be directed to an articulated tip portion comprising a hinge element arranged in a centre plane of the articulated tip part. In one embodiment, the hinge element extends from a proximal end of the articulated tip part to a distal end of the articulated tip part. It should be clear to the person skilled in the art that the different features disclosed in this specification can be combined with these additionally described inventions as well as with other features also described in this specification.

It should be emphasized that the term "comprises/comprising/comprised of" when used in this specification is taken to specify the presence of stated features, integers, steps or components but does not preclude the presence or addition of one or more other features, integers, steps, components or groups thereof. For example, in claim 1 as filed, it is stated that the articulated tip part comprises a passage. This should be understood as comprising at least one passage. Any number of additional passages could also be introduced into the articulated tip part.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

FIGS. 5-8 schematically show four steps in one embodiment of a method of manufacturing an articulated tip part according to the invention.

FIG. 9 shows a schematic exploded view of a distal portion of a second embodiment of an articulated tip part according to the invention.

FIG. 10 shows a schematic side view of a distal portion of the articulated tip part of FIG. 9.

FIG. 11 shows a schematic top view of a distal portion of the articulated tip part of FIG. 9.

FIG. 14 shows a schematic front view of a fifth embodiment of an articulated tip part according to the invention.

FIG. 15 shows a schematic side view of a portion of a bending element for the articulated tip part of FIG. 14.

FIG. 16 shows a schematic side view of a portion of a sixth embodiment of an articulated tip part according to the invention.

FIG. 17 shows a partial schematic side view of a seventh embodiment of an articulated tip part according to the invention.

FIG. 18 shows a partial schematic side view of an eighth embodiment of an articulated tip part according to the invention.

DETAILED DESCRIPTION OF THE EMBODIMENTS

Figure 1:
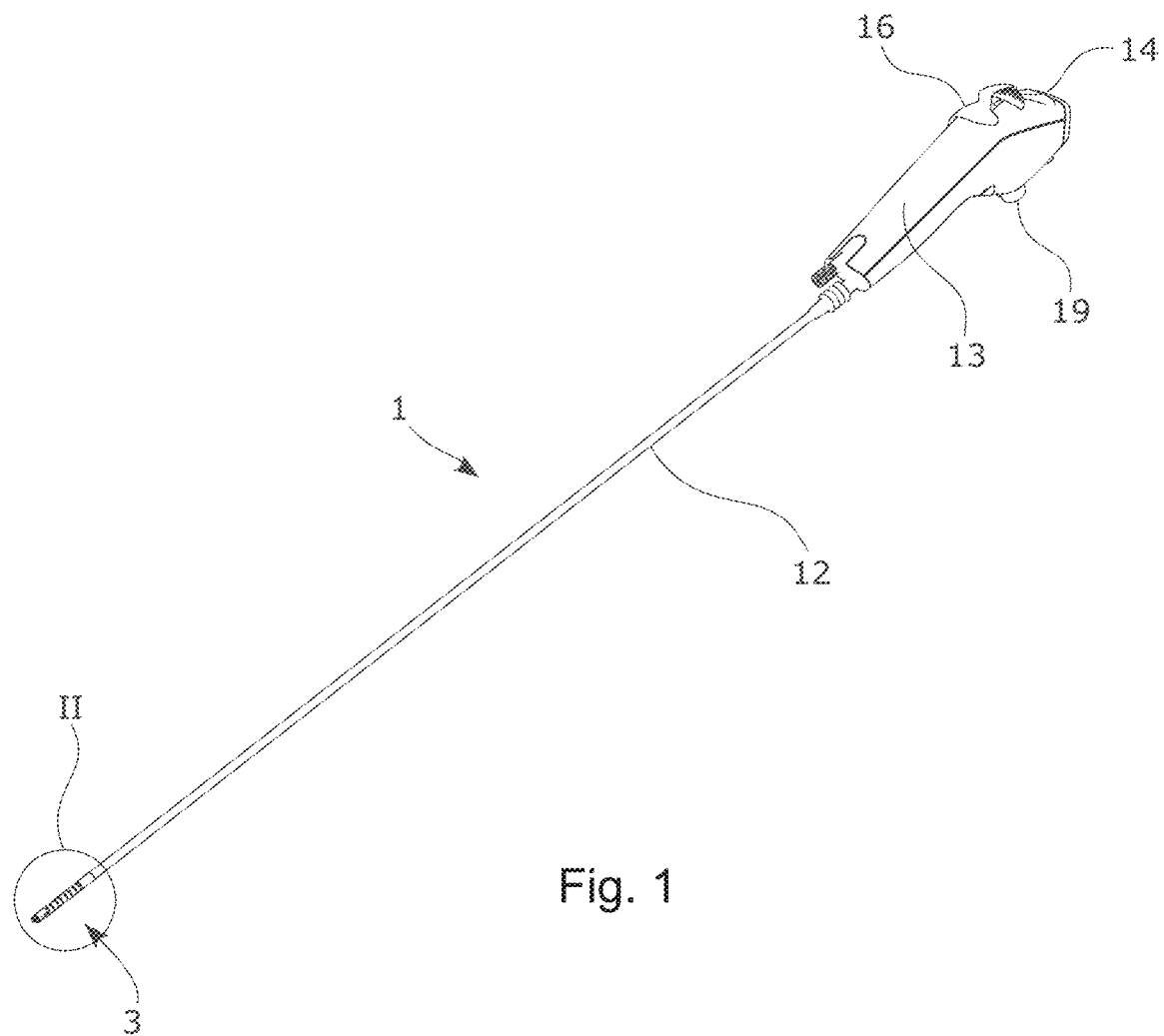
FIG. 1 shows a schematic illustration of one type of endoscope and an example prior art type articulated tip part.

FIG. 1 shows one example of an endoscope 1 as known in the art. The endoscope is disposable and is not designed to be cleaned and reused. The endoscope 1 comprises an elongated insertion tube 12. At the proximal end of the insertion tube 12 an operating handle 13 is arranged. The operating handle 13 has a control lever 14 for manoeuvring an articulated tip part 3 at the distal end of the insertion tube 12 by means of pull wires 15 (visible in FIG. 2 only). The control lever 14 is secured by means of a removable securing clip 16 which is to be removed before use.

Figure 2:
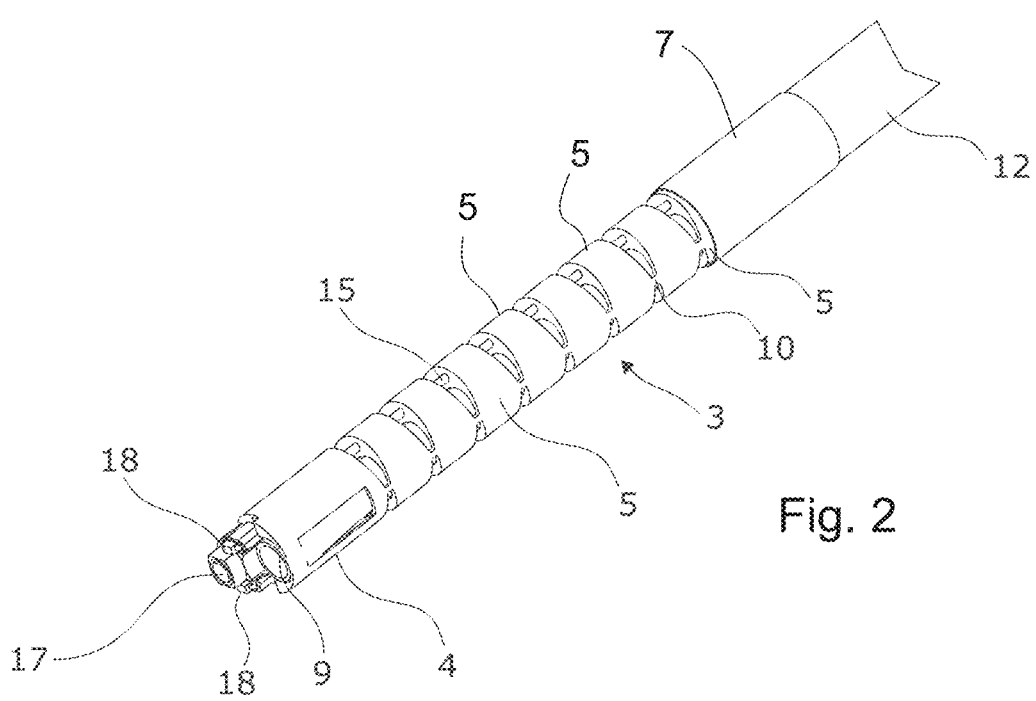
FIG. 2 shows a detailed view of the prior art type articulated tip part of the endoscope shown in FIG. 1 as defined by the area marked by II.

FIG. 2 shows the distal end portion of the insertion tube 12 of FIG. 1 in more detail, especially the articulated tip part 3 is shown in more detail. Some parts, such as an external sheath normally covering the articulated tip part 3, have been removed for clarity.

The articulated tip part 3 is connected to the main body portion of the insertion tube 12 via a connector sleeve 7. The articulated tip part 3 comprises a number of segments 4, 5, 6. More specifically a distal end segment 4, a proximal end segment 6 (hidden under the connector sleeve 7) and a number of intermediate segments 5. In the illustrated embodiments, the number of intermediate segments 5 is eight, but the skilled person will understand that the precise number is less important. The distal end segment 4 comprises a camera 17, light emitting diodes 18 as well as an open end of a tube 9. The tube 9 extends inside the insertion tube 12 all the way from the distal end segment 4 of the articulated tip part 3 to the operating handle 13, so as to form a working channel. The working channel may via a suction port on the handle (not visible) be connected to a standard external source of suction, e.g. wall suction present in a hospital environment, by means of an attached tube (not shown). The external suction may be activated by means of a push-button 19 on the operating handle. The working channel could also be used for other purposes, for example for introducing a tool through the insertion tube 12 and out the distal end segment 4 of the endoscope.

In the articulated tip part 3 shown in FIG. 2, the individual segments 4, 5, 6 are connected together by hinge sections 10 which are integrally moulded together with the segments to form a single integrally moulded element. These hinge sections 10 allow the segments to pivot with respect to each other, but still form an articulated tip part which forms a single element where the individual segments do not need to be individually assembled together in a complicated assembly operation. Furthermore, due to the arrangement of the hinge sections 10, the bending properties of the articulated tip part are controlled such that the tip portion can bend in a controlled manner. In the embodiment shown in FIG. 2, the distal end segment 4 can be displaced upwardly or downwardly by applying tension to respectively the top pull wire 15 or the bottom pull wire (hidden in the figure).

In the prior art solution, due to the fact that the articulated tip part is made as a single integrally moulded element, the bending properties of the articulated tip part are fixed by the choice of the injection moulding material and the design of the hinge sections. Furthermore, additional components of the articulated tip part need to be assembled with the injection moulded articulated tip part after injection moulding. This can add extra steps to the assembly procedure.

Figure 3:
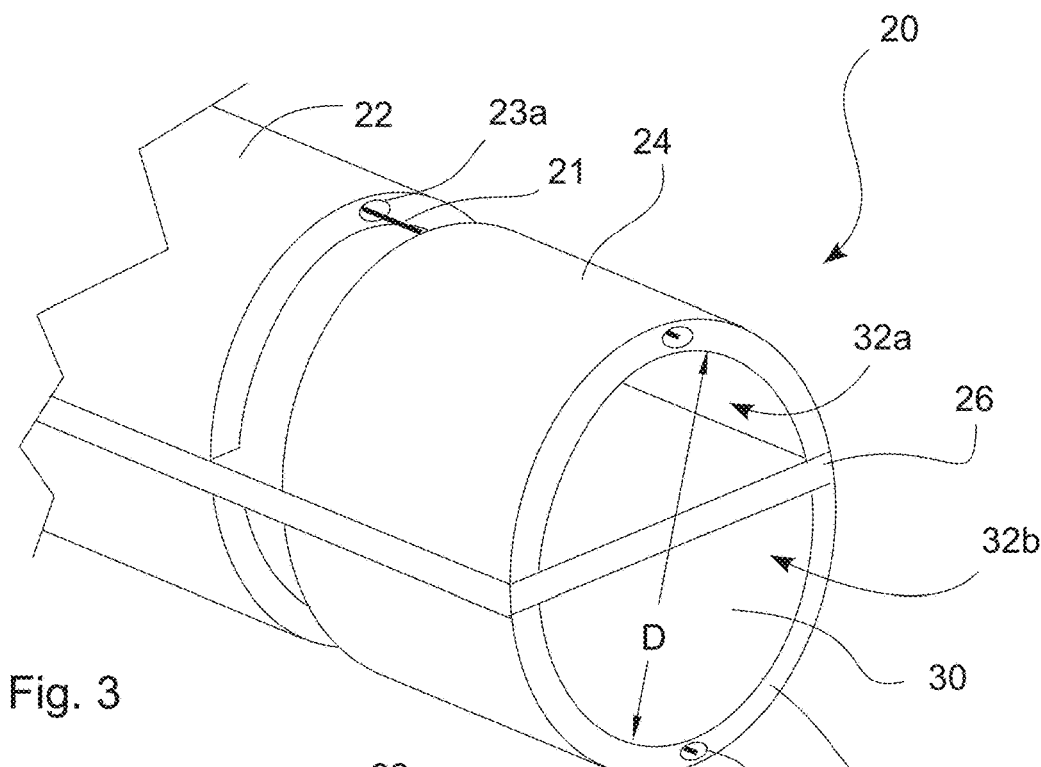
FIG. 3 shows a detailed schematic view of a distal portion of an articulated tip part according to the invention.
Figure 4:
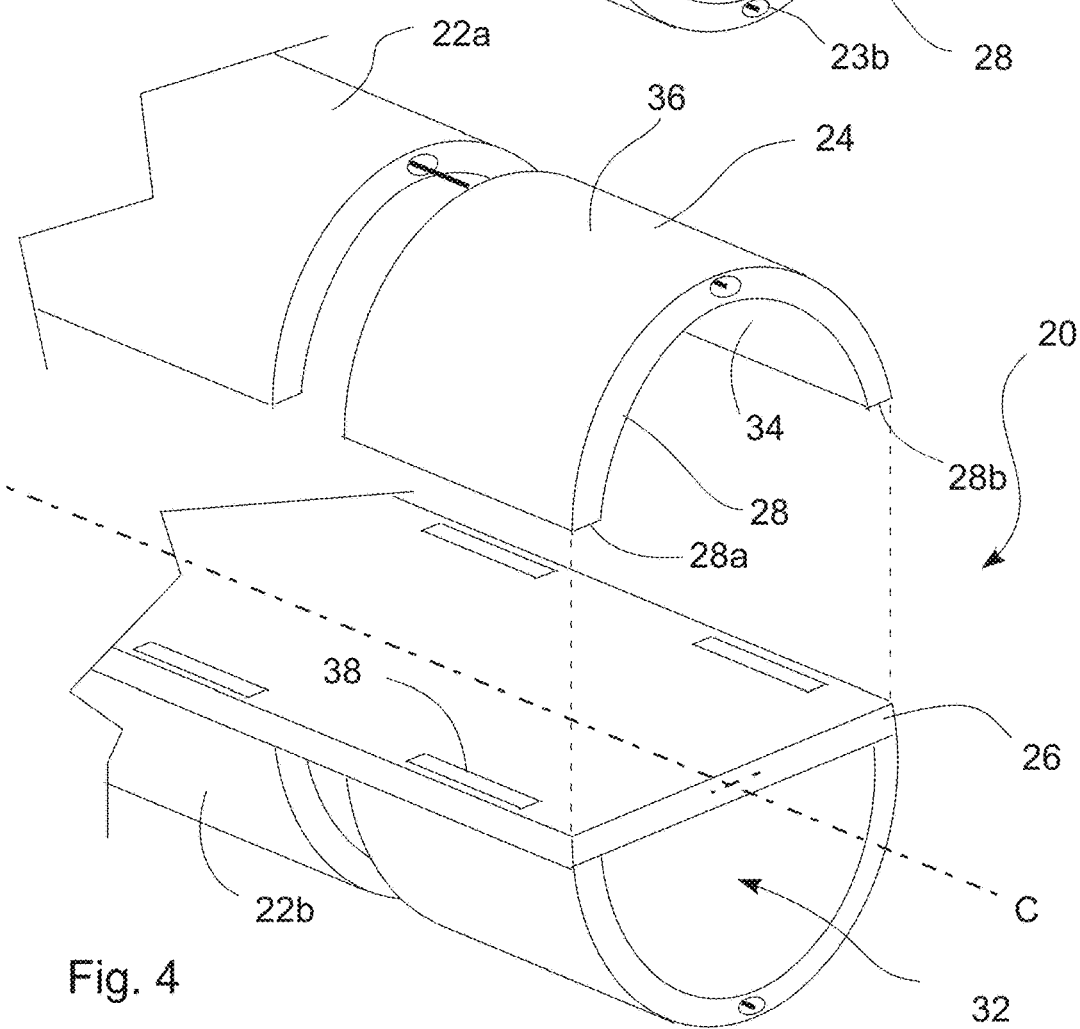
FIGS. 4 to 4E show schematic exploded and assembled views of embodiments of distal portion of articulated tip parts.
Figure 4A:
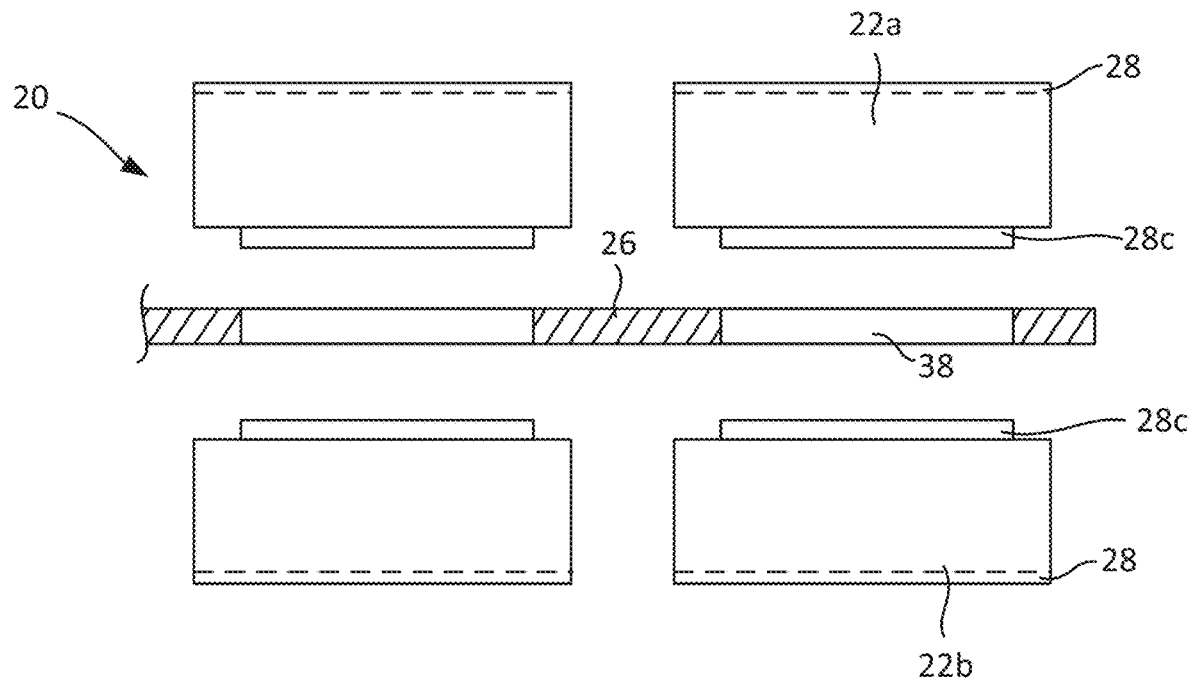
Figure 4B:
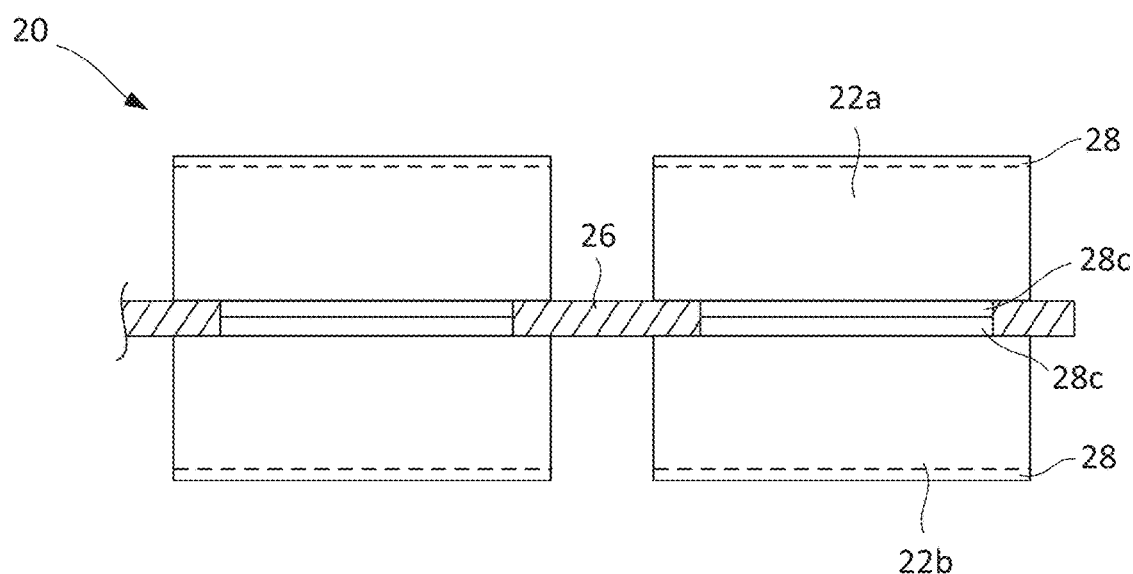

FIGS. 3 and 4 show a distal portion of an embodiment 20 of an articulated tip part according to the invention comprising a number of individual segments 22,24 joined together via a bending element 26 to form an elongated articulated assembly of segments. FIGS. 3 and 4 only show two segments, a distal end segment 24 and an intermediate segment 22. However, as could be imagined by the person skilled in the art, the general functional arrangement of the current embodiment of an articulated tip part 20 is similar to the prior art construction as shown in FIG. 2 where the articulated tip part comprises a proximal end segment (not shown), a number of intermediate segments 22 and a distal end segment 24.

As in the prior art example of FIGS. 1 and 2, the bending of the current embodiment is controlled via pull wires 21 arranged in channels 23a,23b running along the length of the segments. One channel 23a is arranged in the top portion of the segment and one channel 23b is arranged in the bottom portion of the segment. Different arrangements of the channels and the pull wires could be imagined. In one embodiment the channels could be formed as elements fastened to the segments. In another embodiment, the channels could be formed as open grooves formed in an outer or inner surface of the segments. In the case where the channels are formed in the outer surface of the segments as open grooves, the pull wires can be easily arranged in the open grooves and then the open grooves can be closed when the articulated tip part is covered with a covering sleeve (not shown).

It should be noted that the embodiment shown in FIGS. 3 and 4 is shown very schematically and is used to show the principle of the invention in a simple manner. In a real world implementation of the current invention, the actual design would most likely differ from that shown in the figures.

The segments 22,24 of the articulated tip part 20 of the current embodiment are formed as two half shells 22a,22b separated by the bending element 26. In the current embodiment, the bending element 26 is arranged in the form of a metal spring sheet element running along the length of the articulated tip part and essentially centred in the articulated tip part. The two half shells 22a,22b of a segment are fastened to either side of the bending element 26. In the current embodiment, the two half shells are formed as two half portions of a hollow cylinder having a cylindrical cross section. The bending element essentially cuts the cylinder in half. The actual method of assembling/forming the articulated tip part according to this embodiment will be described later on in this specification.

The segments 22,24 each define a wall portion 28 and a hollow portion 30. The individual hollow portions of the individual segments form a passage 32 which runs along the length of the articulated tip art. In the current embodiment, the wall portions each have an inner surface 34 which faces the centre line C of the passage and an outer surface 36 which faces away from the centre line C of the passage. In the current embodiment, the passage 32 has a circular cross section with an inner diameter shown as D in the figures. However, it should be clear to the person skilled in the art that other cross sectional shapes would also be possible within the scope of the invention.

In the current embodiment, the bending element 26 is arranged to span across the passage, from one inner surface to the other inner surface and be embedded in the wall portion of the segments on both sides of the passage 32. In this current embodiment, the bending element cuts the passage 32 into two portions an upper portion 32a and a lower portion 32b. As can be seen from the figures, the bending element 26 is, in the current embodiment, accessible both from the outer surface and the inner surface of the segments. Furthermore, the bending element 26 in the current embodiment could be said to extend from the inside of the wall portion, past the inner surface of the segments and towards the centre line of the passage. Since the bending element in this embodiment is a single element and crosses the entire passage, it could be said that the bending element extends past the inner surface 34 on one side of the passage towards the centre line of the passage and also extends past the opposing inner surface on the other side of the passage again towards the centre line of the passage.

Figure 4C:
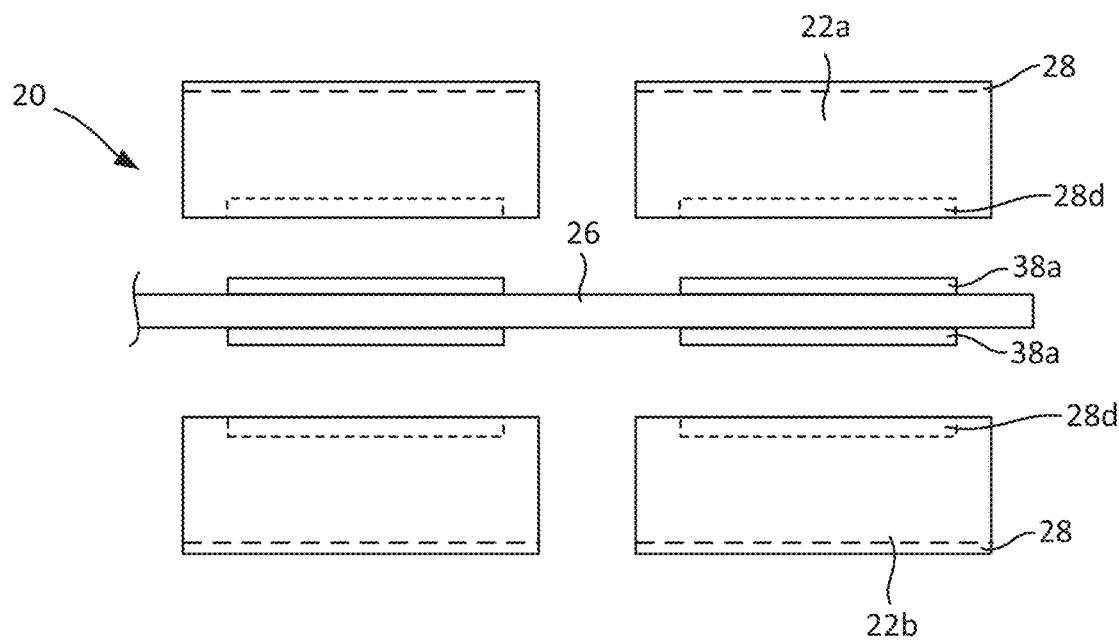
Figure 4D:
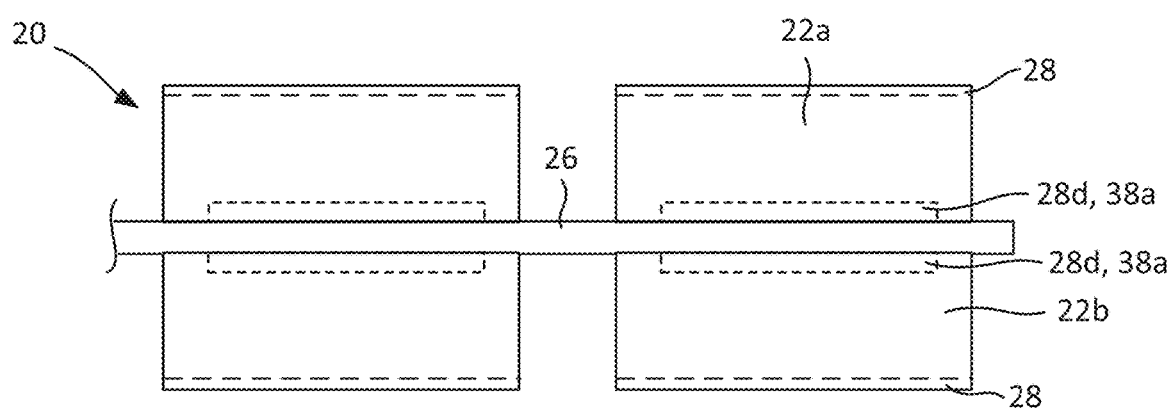
Figure 4E:
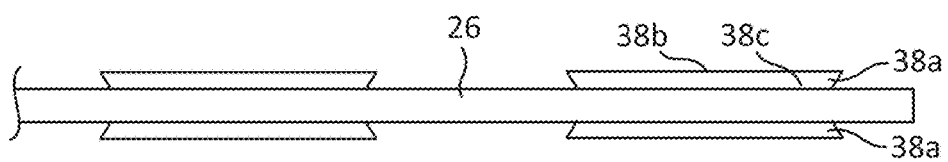

In order to ensure that the segments 22,24 are securely fastened to the bending element 26, through-going recesses 38 are formed in the bending element. The top half 22a of the segment and the bottom half 22b of the segment can be joined together via these through-going recesses 38. The recesses in the current embodiment serve two purposes. A first purpose is to ensure that the segment does not displace along the bending element in a direction parallel to the longitudinal extension of the bending element in an undesired manner. A second purpose is to ensure that the top and bottom halves of the segment are held firmly together about the bending element. Depending on the application and the design of the remainder of the endoscope, the first and/or the second purpose could be omitted in certain embodiments. Likewise, in the current embodiment, a recess is provided in the bending element which provides the more secure connection between the bending element and the segments, however in other embodiments (FIGS. 4C and 4D), protrusions 38a could be arranged on the bending element which extend away from the bending element and which positively and mechanically engage within the material of the segments. For example, a base portion 38c of the protrusion is smaller than the tip portion 38b of the protrusion, as seen in FIG. 4E. In one case it could be said that the protrusions are embedded in the material, e.g. recesses 28d, of the segments. In this way, it becomes difficult to pull the segments away from the bending element since a mechanical connection is made between the segments and the bending element.

FIGS. 5 to 8 schematically show cross sectional views of one method of manufacturing an articulated tip part 20 as shown schematically in FIGS. 3 and 4. It should be noted that in order to simplify the figures, the manufacturing of the channels for the pull wires is not illustrated. However, this should be a detail which the person skilled in the art could implement in a simple manner based on the remaining details presented in this specification together with his or her technical knowledge.

FIG. 5 shows a top half 50 of a mould and a bottom half 52 of a mould. A number of injection nozzles 54 are shown for illustration. The two mould halves are shown drawn apart. Between the two mould halves are shown a top core 56 and a bottom core 58. Between the two cores is shown a bending element 60 in the form of a thin spring sheet foil.

In FIG. 6, the two cores 56, 58 have been moved together to sandwich the bending element and the two mould halves have been moved together to enclose the cores and the bending elements. In this position, the bending element is held firmly in place in the mould. At this time there are no segments at all, just empty cavities 62 surrounding the bending element 60.

In FIG. 7, melted plastic 64 is injected into the cavities 62 through the injection nozzles 54. The cavities 62 are filled with plastic. Once the plastic is cooled, the cores can be withdrawn from the newly formed segments 66 of the articulated tip part 68 and the mould halves can be retracted. The order of retracting the cores and the mould halves depends on the construction of the moulds and cores. The resulting part is shown in FIG. 8.

It should be noted that in the figures, the "slots" 70 between adjacent segments are schematically shown as rectangular slots in cross section. This would not permit a large amount of bending of the articulated tip part before the segments would collide and prevent further bending. However, in other embodiments, the slots could be arranged with a larger angle between adjacent sides and then a larger degree of bending would be available. This is shown with the dashed lines 72 in FIG. 8. The angle can be determined via the internal geometry of the mould.

The manufacturing technique described above is similar to a technique which is known in the art of injection moulding for food and other types of containers. In that area the technology is called In Mould Labelling or IML for short. Instead of printing graphical information on the container, a label can be printed on a sheet of foil first and then inserted into a mould for a container prior to injection moulding the container. The injected plastic is then fused to the material of the foil label. While the two areas have very different purposes and applications, some of the teachings known from the area of IML could be transferred to this new area of manufacturing articulated tip parts for endoscopes.

While the above description has provided one manner of manufacturing the articulated tip part of FIGS. 3 and 4, multiple other methods can also be imagined. One example of another method (not illustrated in the figures) is a method where the bending element is held via a longitudinal clamp which clamps the central portion of the bending element. Pre-manufactured half shells are then applied on each side of the bending element and pressed towards each other to sandwich the bending element between them.

A form of adhesive could be applied between the half segments and the bending element. In one embodiment (not shown), each half segment could have a protrusion which extended halfway into the recess 38 in the bending element. The two half protrusions could meet in the recess and be joined together via a weld or an adhesive. In this way, the top and bottom half segment would be joined together through the bending element. In this way, it is ensured that the two half segments are securely joined together even though they are arranged on either side of the bending element. In another embodiment (not shown) both half segments are provided with corresponding snap elements which engage with each other through a recess in the bending element.

Once the segments are firmly attached to the bending element, the longitudinal clamp could release the bending element and the articulated tip part could be removed from the longitudinal clamp. In another embodiment, the bending element could be made slightly longer than the final length of the articulated tip part. The ends of the bending element could then be held in two clamps, one arranged at the proximal end and one arranged at the distal end of the articulated tip part. The segments could then be attached to the bending element. After attaching all the segments, the clamps could release the bending element and the portions of the bending element which are protruding from the distal and proximal ends of the articulated tip part could be trimmed off. In a similar method, instead of holding onto proximal and distal portions extending past the ends of the articulated tip part, the bending element could be made wider than the final width of the articulated tip part. The sides of the bending element could therefore be held in clamps and then after assembly of the segments, the portions of the bending element protruding past the sides of the articulated tip part could be trimmed off.

In another method (not shown) the bottom half shell could be held in a clamp and adhesive could be applied to the upward facing edge of the half shell. Then the bending element could be applied on the upward facing edge of the half shell. Then the top half shell could be mounted on the bending element thereby sandwiching the bending element between the bottom and top half shells.

FIGS. 9 to 11 show another embodiment 80 of a portion of an articulated tip part for an endoscope. This embodiment is essentially identical to the embodiment shown in FIGS. 3 and 4, however the bending element 82 has been provided with extra cut-outs 84 between adjacent segments 86. These cut-outs are made in the bending element and extend from a location close to the centre of the bending element and out towards the side edge of the bending element. This allows the articulated tip part to bend about one more axis in comparison to the embodiment shown in FIGS. 3 and 4. A first axis A is parallel to the plane of the bending element 82 and perpendicular to the longitudinal extension of the bending element. This is the same as with the articulated tip part shown in FIGS. 3 and 4. The second axis B is perpendicular to the plane of the bending element. In the previous embodiment, the cross sectional moment of inertia of the bending element about the second axis was large. By providing the cut-outs 84 in the bending element, the cross sectional moment of inertia of the bending element about the second axis B at the location of the cut-outs is decreased significantly.

In the embodiment shown in FIG. 9, the cut-outs are centred about the centre axis of the articulated tip part. However, it could also be imagined that the cut-outs were offset towards one side of the articulated tip part. For example the cut-out on the left side could be shorter than the cut-out on the right side. In this way, the bending properties could be adjusted and the bending profile to the left could be different than the bending profile to the right.

FIG. 10 shows a side view of the articulated tip part of FIG. 9. In this side view, the tip can move up and down (as in FIGS. 3 and 4) and in and out of the page (new axis). FIG. 11 shows a top view of the articulated tip part of FIG. 9. In this top view, the tip can move into and out of the page (as in FIGS. 3 and 4) and also up and down (new axis). In this embodiment, four pull wires would typically be used to control the bending. Two wires located in the top/bottom portion would be used to control the bending about the old axis as in FIGS. 3 and 4 and two wires located in the left/right portion would be used to control the bending about the new axis.

Figure 12:
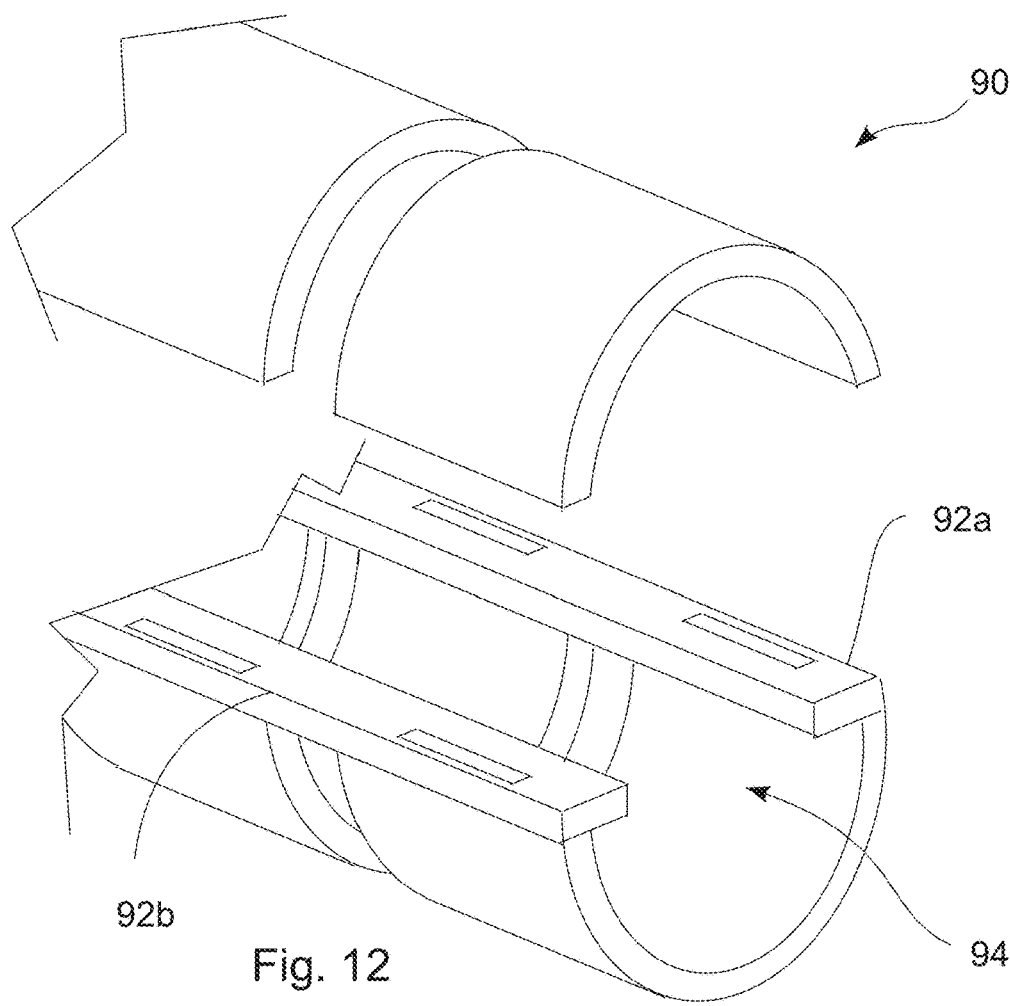
FIG. 12 shows a schematic exploded view of a third embodiment of a distal portion of an articulated tip part to the invention.

FIG. 12 shows another schematic embodiment 90 of a distal portion of an articulated tip part of an endoscope. This embodiment is for the most part the same as the embodiment of FIGS. 3 and 4, however, instead of a single bending element arranged in the middle of the articulated tip part, two separate bending elements 92a,92b are arranged, one running along each of the two sides of the articulated tip part. In this way, the central passage 94 running along the length of the articulated tip part is less obstructed and there is more room for additional accessories, for example electrical signal cables, working channels, light guides, etc.

Figure 13:
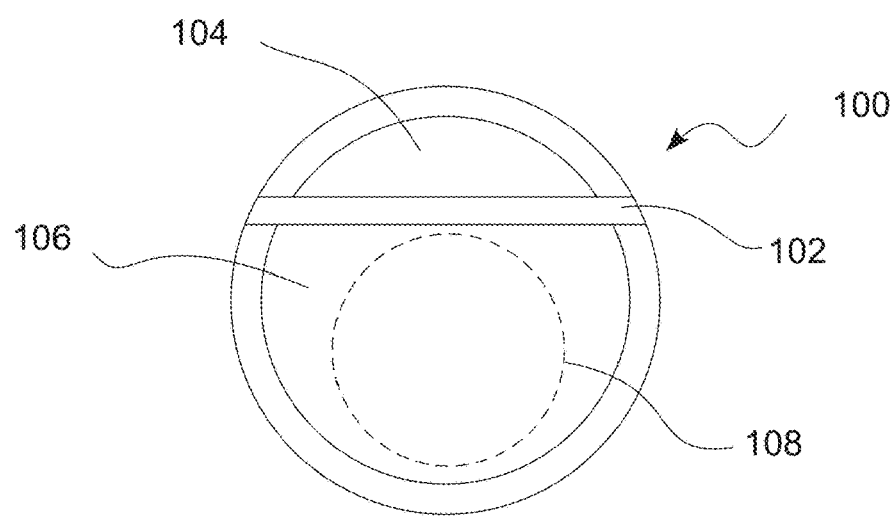
FIG. 13 shows a schematic front view of a fourth embodiment of an articulated tip part according to the invention.

FIG. 13 shows another schematic embodiment 100 of a distal portion of an articulated tip part. In this case, the bending element 102 is arranged offset from the central axis of the articulated tip part. In this way, instead of two identical channels on each side of the bending element, in this embodiment, there are two different sized channels, a first channel 104 arranged above the bending element and a second channel 106 arranged below the bending element. In this case, the second channel 106 is much larger than the first channel 104. This means that the second channel can accommodate larger accessories, for example a tube 108 forming a working channel having a greater diameter.

Placing the bending element offset from the central axis will have an effect on the bending properties of the articulated tip portion. In certain cases, this can be accepted and in other cases it is actually desired to provide non-symmetrical bending performance. In other cases where non-symmetrical bending performance is not desired this can be compensated for, for example by adjusting the geometrical design of the bending element, the geometrical design of the segments of the articulated tip part, etc.

FIG. 14 shows another schematic embodiment 110 of a distal portion of an articulated tip part. In this case, instead of a flat bending element as in the previous embodiments, in this embodiment, the bending element 112 has a central portion which is formed as an elongated half cylindrical portion 114. In this way, a channel is formed in the central area of the articulated tip part in which cables, etc can be arranged and protected. This also provides a greater available area on one side of the bending element. It should be clear that cross sections other than cylindrical half portions could be imagined.

By forming the bending element as a non-planar element, the cross sectional inertia of the bending element about the main bending axis of the articulated tip part will increase, thereby making the articulated tip part more difficult to bend. In certain cases, this could be acceptable, however, in other cases, this can be compensated for by providing areas of the bending element with a reduced stiffness. In one example, as shown in FIG. 15, cut-outs 116 are made in the central cylindrical portion 114 of the bending element 112. The cut-outs are arranged between the segments of the articulated tip part. The cross-sectional inertia of the bending element at the location between the segments will therefore be reduced. In another example (not shown), instead of providing cut-outs, the geometry of the bending element at the location between the segments could be adjusted, for example by reducing the wall thickness of a portion of the bending element. Or in another example (not shown), the stiffness properties of the material could be adjusted at certain locations, for example by appropriate heat treatment or other treatment.

FIG. 16 shows another schematic embodiment 120 of a portion of an articulated tip part. In this case, the thickness of the bending element 122 decreases from the proximal end segment 124 to the distal end segment 126. Thus, the bending ability increases towards the distal end, which, in turn can increase manoeuvrability. In another embodiment, not shown, the bending element could be made of a laminated element which has sections of different thicknesses. For example, the proximal end portion of the bending element could comprise 8 layers and the distal end could comprise only 2 layers. In this case, the different elements of the laminated element can have different lengths along the length of the articulated tip part. In another embodiment (not shown), instead of providing a bending element with different thicknesses along the extension of the bending element, a bending element could be provided with cut-outs along the longitudinal extension where the shape and/or dimension of the cut-outs varies along the length of the bending element so that the bending properties are variable along the length of the bending element.

FIG. 17 shows another schematic embodiment 130 of a portion of an articulated tip part. In this case, the bending element 132 is arranged with an embedded light transmitting portion 132. A light source 134 is arranged at the proximal end of the articulated tip part and light is transmitted through the light transmitting portion of the bending element 132. Light 136 is then emitted from the distal portion of the bending element. In one embodiment, the bending element itself is made up of a light transmitting element itself. In another embodiment, the bending element comprises a light transmitting element embedded in the bending element itself. In addition to the light transmitting function, the articulated tip part also comprises a camera device 138 and a wire 139 for transmitting data from the camera device along the articulated tip part.

FIG. 18 shows another schematic embodiment 140 of an articulated tip part. In this embodiment, the bending element 142 comprises a flexible printed circuit board 142 as a component of the bending element itself. In one embodiment, the bending element is itself a flexible printed circuit board. In another embodiment, the flexible printed circuit board can be arranged as one layer of the bending element.

In the embodiment shown, a camera device 144 and a light source 146 are arranged in the distal end segment 148. Power and data is transmitted to/from the camera device and the light source via the flexible printed circuit board integrated into the bending element. In this way, it is not necessary to run cables and wires along the articulated tip part for data/power transmission. In certain cases, the flexible printed circuit board could be arranged only in the articulated tip part and wires connected to the flexible printed circuit board could run from the proximal end of the articulated tip part to the proximal end of the insertion tube of the endoscope. However, in other embodiments, a flexible printed circuit board could be provided which runs from the handle all the way to the distal end of the articulated tip part. The distal portion of the flexible printed circuit board could then be integrated into the articulated tip part as described above. In general, this could be true for other functional elements as well. For example, a light guide element could be arranged just in the articulated tip part, or a longer light guide element could be arranged which extends from the handle all the way to the distal end of the articulated tip part and a distal portion of the light guide could be integrated with the articulated tip part as a bending element. In another example the pull wires for controlling the articulated tip part could be arranged in tubular elements which are at least the length of the articulated tip part and which could be integrated directly into the articulated tip part during the manufacturing procedure of the tip part.

It is to be noted that the figures and the above description have shown the example embodiments in a simple and schematic manner. Many of the specific mechanical details have not been shown since the person skilled in the art should be familiar with these details and they would just unnecessarily complicate this description. For example, the specific materials used and the specific injection moulding procedures have not been described in detail since it is maintained that the person skilled in the art would be able to find suitable materials and suitable processes to manufacture the articulated tip part according to the current invention.

I claim:

1. An articulated tip part suitable for an endoscope, where the articulated tip part comprises:

segments including a distal end segment, a proximal end segment, and an intermediate segment having a first part and a second part, the intermediate segment arranged between the distal end segment and the proximal end segment, said segments being joined together to form an articulated assembly of segments;

a passage running along a length of the articulated tip part;

a bending element having a first side opposite a second side, said bending element being fastened to at least two of the segments and being arranged along a path which is essentially parallel to a centerline of the articulated tip part, wherein the bending element comprises recesses having a closed perimeter, the recesses configured to positively and mechanically engage with material of the intermediate segment to fasten the first part to the first side and the second part to the second side, of the bending element wherein the recesses are arranged to pass through the bending element such that the material of the segments passes through the bending element and the bending element completely surrounds the material of the segments passing through the bending element.

2. The articulated tip part of claim 1, wherein the bending element is fastened to at least three segments, and wherein the segments comprise an inner surface facing the centerline of the passage and an outer surface facing away from the centerline of the passage, said bending element being accessible via the inner and/or the outer surface.

3. The articulated tip part of claim 2, wherein the bending element extends past the inner surface of the segments and towards the centerline of the passage and/or past the outer surface of the segments and away from the centerline of the passage.

4. The articulated tip part of claim 2, wherein the bending element is arranged such that one of the at least two segments is the proximal segment and/or such that one of the at least two segments is the distal segment.

5. The articulated tip part of claim 1, wherein the first part and the second part are connected to each other via the recesses which pass through the bending element.

6. The articulated tip part of 1, wherein a dimension of the bending element which is perpendicular to a longitudinal extent of the bending element is greater than a minimum inside diameter of the passage.

7. The articulated tip part of claim 1, wherein the bending element comprises a light guide or a flexible printed circuit board, fastened to and running along a length of the bending element, or wherein the bending element comprises electronic components fastened to and spaced along the length of the bending element.

8. The articulated tip part of claim 1, wherein a stiffness of the bending element varies along a longitudinal extent of the bending element.

9. The articulated tip part of claim 8, wherein a thickness of the bending element perpendicular to the longitudinal extent of the bending element and/or a moment of inertia of the bending element changes along the length of the bending element.

10. The articulated tip part of claim 1, wherein the bending element comprises spaced apart weakened portions arranged along a longitudinal extent of the bending element and said weakened portions have a stiffness which is less than a stiffness of a remaining portion of the bending element.

11. The articulated tip part of claim 10, wherein said weakened portions allow pivotal motion of the segments in a plane parallel to the bending element and/or in a plane perpendicular to a main bending plane of the tip part.

12. Endoscope comprising the articulated tip part of claim 1.

13. The articulated tip part of claim 1, wherein the first part and the second part each have an arcuate wall ending in a first contact surface and a second contact surface, the first contact surface and the second contact surface extending between a proximal edge and a distal edge of the arcuate wall, wherein after construction the first contact surface of the first part is adjacent the first contact surface of the second part with the bending element extending at least partially therebetween.

14. The articulated tip part of claim 1, wherein the bending element comprises an elongate substantially flat surface extending between at least three of the segments.

15. The articulated tip part of claim 1, wherein a thickness of the bending element decreases in the distal direction along a longitudinal extent of the bending element.

16. The articulated tip part of claim 15, wherein the bending element is comprised of a material different than the material of the intermediate segment.

17. The articulated tip part of claim 1, wherein the bending element comprises a non-planar cross-section, the cross-section taken transversely to a longitudinal extent of the bending element.

18. An articulated tip part suitable for an endoscope, where the articulated tip part comprises:

segments including a distal end segment, a proximal end segment, and an intermediate segment having a first part and a second part, the intermediate segment arranged between the distal end segment and the proximal end segment, said segments being joined together to form an articulated assembly of segments;

a passage running along a length of the articulated tip part;

a bending element having a first side opposite a second side, said bending element being fastened to at least two of the segments and being arranged along a path which is essentially parallel to a centerline of the articulated tip part, wherein the bending element comprises protrusions extending perpendicularly to a plane parallel to a main surface of the bending element, the protrusions configured to positively and mechanically engage with material of the intermediate segment to fasten the first part to the first side and the second part to the second side, of the bending element, wherein the protrusions of the bending element extend into the material of the intermediate segment, and wherein the protrusions comprise a base portion that is smaller than a tip portion thereof.

* * * * *